(12) United States Patent
Brown

(10) Patent No.: US 7,318,438 B2
(45) Date of Patent: Jan. 15, 2008

(54) INTERNAL NASAL DILATOR AND MEDICINE DELIVERY METHOD

(76) Inventor: Thomas W. Brown, 5811 Widmer, Shawnee, KS (US) 66216

(*) Notice: Subject to any disclaimer, the term of this patent is extended or adjusted under 35 U.S.C. 154(b) by 384 days.

(21) Appl. No.: 11/111,137

(22) Filed: Apr. 22, 2005

(65) Prior Publication Data

US 2006/0185677 A1    Aug. 24, 2006

Related U.S. Application Data

(63) Continuation-in-part of application No. 11/065,677, filed on Feb. 24, 2005, now Pat. No. 7,055,523.

(51) Int. Cl.
*A61M 16/00* (2006.01)
*A61M 15/08* (2006.01)
*A61F 5/08* (2006.01)

(52) U.S. Cl. ............ 128/206.11; 128/207.18; 606/204.45

(58) Field of Classification Search ............ 128/200.26, 128/204.12, 206.11, 206.12, 206.18, 206.27, 128/207.13, 207.18, 848, 858; 606/191, 606/198, 199, 204.45; 604/93.01, 94.01
See application file for complete search history.

(56) References Cited

U.S. PATENT DOCUMENTS

| | | | |
|---|---|---|---|
| 513,458 | A | 1/1894 | Dayton |
| 1,069,459 | A | 8/1913 | Myles |
| 1,077,574 | A | 11/1913 | Woodward |
| 1,255,578 | A | 2/1918 | Boxley |
| 1,672,591 | A | 6/1928 | Wells |
| 1,709,740 | A | 4/1929 | Rogers |
| 2,243,360 | A | 5/1941 | Slatis |
| 2,674,245 | A | 4/1954 | Tanditter |
| 3,710,799 | A | 1/1973 | Caballero |
| 4,267,831 | A | 5/1981 | Aguilar |
| 4,759,365 | A | 7/1988 | Askinazy |
| 5,479,944 | A | 1/1996 | Petruson |
| RE35,408 | E | 12/1996 | Petruson |
| 5,922,006 | A | 7/1999 | Sugerman |
| 7,055,523 | B1 * | 6/2006 | Brown ............ 128/206.11 |
| 7,108,198 | B2 * | 9/2006 | Altadonna, Jr. ............ 239/34 |
| 2004/0059368 | A1 * | 3/2004 | Maryanka ............ 606/191 |
| 2004/0237967 | A1 | 12/2004 | Davis |

* cited by examiner

*Primary Examiner*—Teena Mitchell
(74) *Attorney, Agent, or Firm*—Spencer Fane Britt & Browne LLP

(57) ABSTRACT

A method of making an internal nasal apparatus (10) configured to retain and deliver a quantity of compound within the nose of a user over a minimum period.

20 Claims, 6 Drawing Sheets

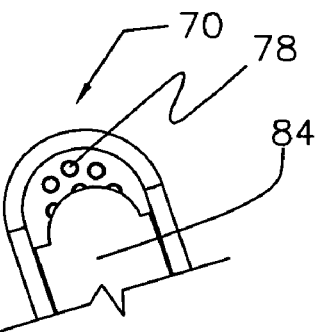
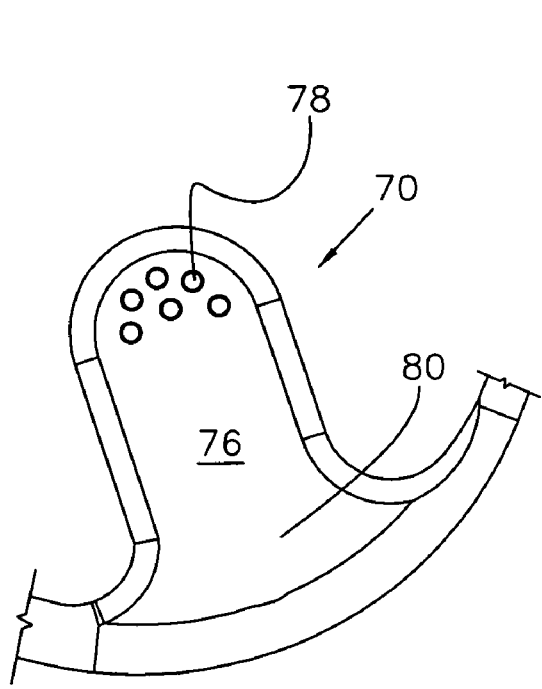
FIG. 5
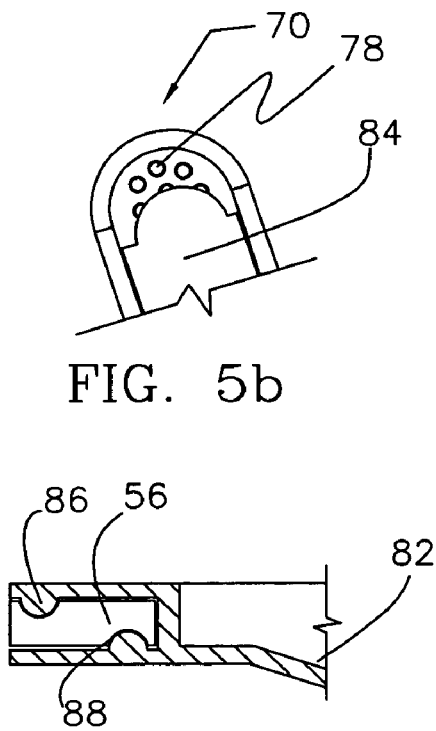
FIG. 5b
FIG. 5a
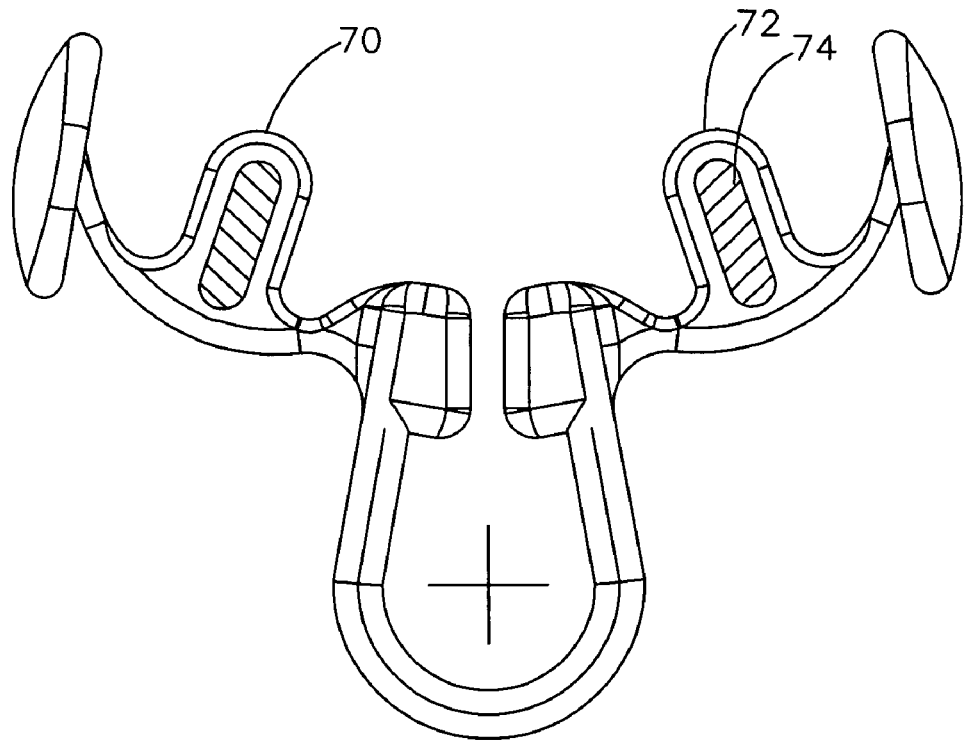
FIG. 4

INTERNAL NASAL DILATOR AND MEDICINE DELIVERY METHOD

RELATED APPLICATIONS

The present application is a continuation-in-part and claims priority benefit with regard to all common subject matter U.S. patent application Ser. No. 11/065,677, now U.S. Pat. No. 7,055,523, filed Feb. 24, 2005, and issued Jun. 6, 2006. The identified patent is hereby incorporated by reference into the present application.

BACKGROUND OF THE INVENTION

1. Field of the Invention

The present invention relates generally to mechanisms and methods for dilating nasal passages and delivering medications, drugs, or other compounds. More particularly, the present invention concerns an improved internal nasal dilator for increasing nasal breathing efficiency and for delivering a time-released compound within the nostrils of a user, and a method of making the same.

2. Discussion of the Prior Art

It is well documented that collapsed or constricted nasal passageways result in a multitude of bodily problems, including sleep apnea, sinus infection, and other respiratory ailments. Another well-known problem associated with reduced passageways is snoring. In this condition, audible sounds produced by the vibration of the soft palate and internal nasal structure can be a nuisance to persons within hearing distance and can affect the quality of sleep of the snoring person.

To alleviate these ailments and conditions, a variety of nasal dilator mechanisms, including external and internal versions, have been developed over time. Prior art external nasal dilators often take the form of an adhesive strip that is worn on an exterior portion of the nose and function to lift the walls of the nasal passages. Unfortunately, the frictional grab-strength required by these external dilators often causes discomfort or damage to the skin and soft facial tissues of the user. Furthermore, external placement of these dilators exposes them to a variety of forces arising from rubbing against objects, such as pillows, that can prematurely dislodge the dilator.

Prior art internal nasal dilators function within the nostrils of the user, and, as a result, are not subject to being prematurely dislodged by external forces. These dilators are typically held in place by a clamping mechanism that pinches the septum generally along two contact points, or by stretching the nostrils enough to result in a compressive force on the dilator sufficient to hold it in place. The non-adjustability of these dilators, however, are problematic given that there are an infinite number of sizes and shapes of human nostrils. The pinching mechanisms of these dilators are also problematic in that they cause discomfort to the user, including pain where prolonged usage is necessary. The fact that some of these internal dilators must stretch the nostrils to a greater extent than is necessary to simply dilate the nostril also causes further discomfort and noticeability.

The prior art also includes nasal mechanisms combined with gaseous delivery systems for providing a measured flow of medicine to the user. These combinations, however, typically require that an external source be securely connected to the mechanism during usage, which makes them problematically cumbersome. Connection to an external source also reduces comfort by limiting the user to certain positions in order to ensure proper operation, which may further inhibit the user from sleeping. Furthermore, these combinations include notoriously complex mechanical, electrical, or pneumatic components that make their manufacture time-consuming and expensive.

Due to these and other problems and limitations in the prior art, an improved nasal dilator and delivery mechanism is needed.

SUMMARY OF THE INVENTION

The present invention overcomes the problems and limitations in the prior art by providing an improved internal nasal dilator for increasing nasal breathing efficiency and for delivering a time-released compound within the nostrils of a user, and a method of making the same.

A first aspect of the invention concerns an internal nasal dilator adapted for use within a nose having first and second nostrils separated by a septum, with each of the nostrils defining in part an internal nasal passageway and an interior outer wall surface generally opposite the septum. The dilator comprises a generally U-shaped clip configured to contact and apply a holding force to the septum when the dilator is donned. The clip is further configured to contact the septum along first and second planar engaging surfaces. The dilator also includes first and second nostril expanders, wherein each of the expanders further include a nostril engaging element configured to overlay and conform to a portion of the interior outer wall surface of said first or second nostril, and an arm interconnecting the nostril engaging element and clip. The element, arm and clip are cooperatively configured to exert a force upon said portion of the interior outer wall surface.

A second aspect of the invention concerns an internal nasal apparatus adapted for use within a nose having first and second nostrils separated by a septum, each of the nostrils defining in part an internal nasal passageway, an outlet, and an interior outer wall surface generally opposite the septum. The apparatus comprises a holding element configured to contact and apply a holding force to the nose so as to secure the apparatus at least partially within both nostrils when the apparatus is donned, and first and second delivery elements. Each of the delivery elements is configured to retain a quantity of a medicine, drug, or other compound within the nasal passageway of one of said first or second nostrils and to discharge the quantity within the nasal passageway at a minimum distance from the outlet of said one of said first or second nostrils over a minimum period of time.

A third aspect of the present invention concerns a method of increasing the efficiency of nasal breathing and delivering a compound within a nose having a septum and first and second nostrils, wherein each nostril defines an inner outer wall surface, and a nasal passageway. The method comprises the steps of engaging and applying outward forces to the inner outer wall surfaces, and engaging and applying compressive forces to the septum, so as to retain the nostrils in an expanded open position; and retaining a quantity of a medicine, drug, or other compound within the nostrils and gradually discharging the quantity at a minimum distance within the nasal passageway and over a minimum period of time.

The present invention also concerns an improved method of making the internal nasal apparatus and compound delivery system. More particularly, the present invention concerns a method of making an internal nasal apparatus adapted for retaining and delivering a quantity of compound within the nose of a user. The method comprises the steps of providing an internal nasal apparatus having first and second delivery elements configured to be inserted within the nose of the user, providing a quantity of compound containing a desired agent, providing first and second mold cavities, or negative molds, configured to receive said first and second delivery elements and said quantity of compound, inserting at least a portion of said first and second delivery elements within the molds, inserting said quantity of compound within the molds and adjacent said portion, adhering the compound to said portion, and removing said molds to expose said quantity of compound.

Other aspects and advantages of the present invention will be apparent from the following detailed description of the preferred embodiment and the accompanying drawing figures.

BRIEF DESCRIPTION OF THE DRAWING FIGURES

Several embodiments of the invention are described in detail below with reference to the attached drawing figures, wherein:

FIG. 4 is a plan view of an internal nasal dilator shown in FIGS. 1 through 3, having two compound delivery elements;

FIG. 5 is an enlarged fragmentary plan view of the dilator, particularly illustrating a compound delivery element;

FIG. 5a is an enlarged fragmentary cross-sectional view of a removably fixed connection between a compound delivery element and an arm in accordance with a preferred embodiment of the present invention;

FIG. 5b is an enlarged fragmentary plan view of the compound delivery elements, particularly showing the adjustable overlay;

DETAILED DESCRIPTION OF THE PREFERRED EMBODIMENTS

With reference to the figures, a nasal dilator, delivery mechanism, and method of making the same are herein described, shown, and otherwise disclosed in accordance with the preferred embodiments of the present invention. More specifically, the present invention concerns an improved internal nasal dilator for increasing nasal breathing efficiency and for delivering a time-released compound within the nostrils of a user, and a method of making the same.

Figure 1:
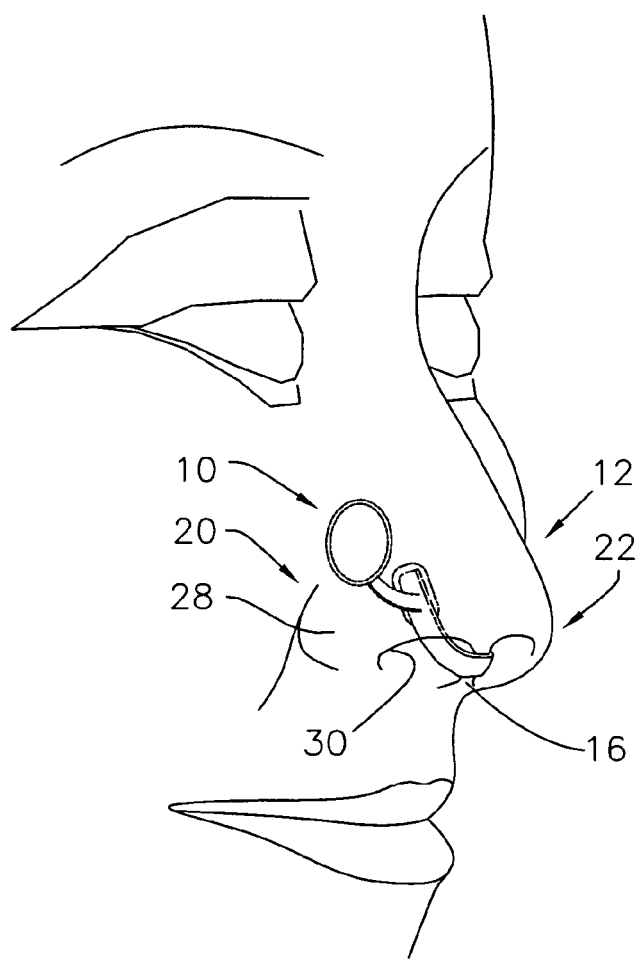
FIG. 1 is a perspective view of an internal nasal dilator constructed in accordance with a first preferred embodiment of the present invention, particularly illustrating the dilator being donned by a human user.

As best shown in FIG. 1, a first preferred embodiment of the present invention concerns an improved internal nasal dilator 10 adapted for use predominately within a nose. Although further described herein with respect to a human user, the present invention may be modified in size and shape to properly function within the noses of a variety of animals. For example, the structure of the dilator 10 could be elongated and broadened for equine or canine usage without departing from the present invention. It is also within the present invention to modify the configuration of the dilator, so long as compound storage and delivery occurs at the prescribed minimum distances within the nose.

Figure 1A:
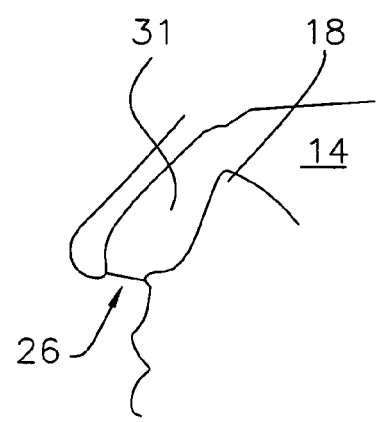
FIG. 1a is a schematic side-elevational view of the inner-structure of the human nose.
Figure 1B:
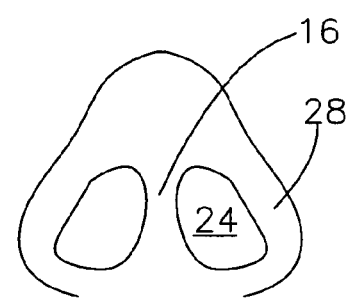
FIG. 1b is an interior view of the human nose.

Turning first to FIGS. 1, 1a, and 1b, the human olfaction organ is divided into an external portion, i.e. the visible projecting portion 12, to which the term "nose" is restricted herein, and an internal portion, consisting of two principal cavities, or nasal fossae 14, separated from each other by a vertical septum 16. Each of the nasal cavities 14 fluidly communicates with ambient air conditions through a constricted orifice, or ostium internum 18, located at the union of the two portions. The nose 12 further presents first and second nostrils 20,22 also separated by the septum 16. Each of the nostrils 20,22 define in part an internal nasal passageway 24, a nasal outlet 26, and a resistively elastic outer wall 28. The internal nasal passageway 24 as used herein, is limited to the vestibules formed by the nose 12, and does not include the nasal cavities 14 and other inner workings of the organ. The passageway distance is defined as the linear distance along the longitudinal axis of the vestibules as measured from the outlet 26 to the orifice 18. The outer wall 28 presents an interior outer wall surface 30 generally opposite the septum 16. Finally, a mucosal lining 31 further described herein overlays a significant portion of the nasal passageways 24 and cavities 14.

Figure 3:
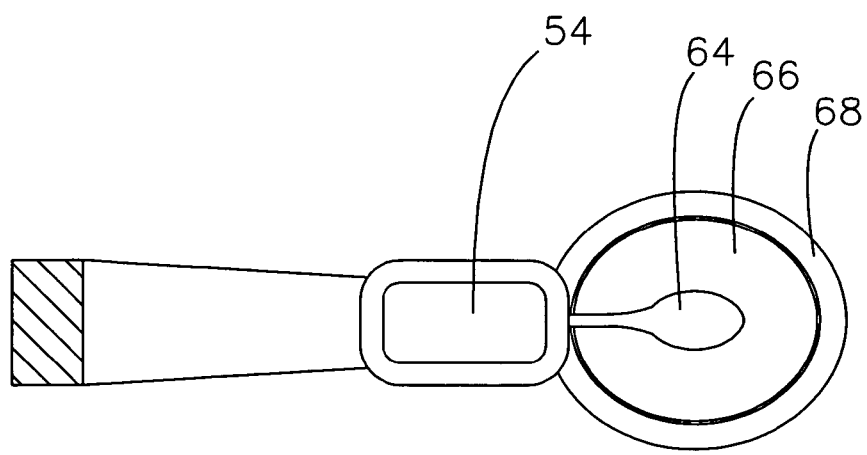
FIG. 3 is a cross-sectional view of the dilator taken along the line A-A shown in FIG. 2, particularly illustrating the connection between the disk and arm.

As illustrated in FIGS. 2 through 5, the improved internal nasal dilator 10 includes a septum constricting clip 32, and left and right nasal expanders 34,36 (i.e., dilating elements). The septum constricting clip 32 is configured to retain and apply a holding force to a portion of the septum 16. The preferred clip 32 presents a symmetric generally U-shaped body having constant depth and thickness and defining interior and exterior clip surfaces 44,46. The clip 32 is formed by first and second linear portions 38,40 and a bent portion 42 interconnecting the linear portions 38,40. The bent portion 42 is configured so as to place the linear portions 38,40 generally adjacent to the septum 16 by orienting the linear portions 38,40 generally towards the septum 16. Thus, the linear portions 38,40 are configured to converge as they approach their distal ends spaced from the bent portion 42. More preferably, to minimize internal obstruction, at least a section of the linear portions 38,40 present tapered depths, as shown in FIG. 3. In this arrangement, the depth of the clip 32 gradually decreases as the linear portions 38,40 approach their distal ends.

Improved septum engaging pads 48,50 are attached to the clip 32 adjacent the distal ends and along the interior clip surface 44. Each of the pads 48,50 are configured to engage the septum 16 along planar innermost clip surfaces 52,54, so that the septum 16 is not pinched by point or minimal area contact during usage. Each of the pads 48,50 presents a trapezoidal shape, wherein the innermost clip surfaces 52,54 are oriented generally parallel to the septum 16 in the normal position (see FIG. 2). More preferably, each of the surfaces 52,54 presents a surface area not less than 0.2 square centimeters, and most preferably, not less than 0.5 square centimeters. Finally, so as not to damage the mucosal lining 31 during placement and removal, the preferred pads 48,50 present chamfered or filleted edges. It is believed that this improved design significantly increases comfort to the user, while stimulating the trigeminal nerve and dilating the nasal passage.

Each of the nasal passage expanders 34,36 are virtually identically configured and, therefore, only nasal passage expander 34 will be described in detail, with the understanding that nasal passage expander 36 is similarly constructed. The expander 34 is configured to retain the outer wall 28 of the nostril 20 in an open or dilated position as shown in FIG. 1. In a first preferred embodiment of the present invention, the expander 34 generally includes an arm 56 spaced from the nostril and a nostril engaging disk 58 (see FIGS. 2 through 4). By engaging only the interior outer wall surface 30 with the disk 58, the improved expander 34 is configured to minimally engage the nostril 20, thereby reducing noticeability.

Figure 2:
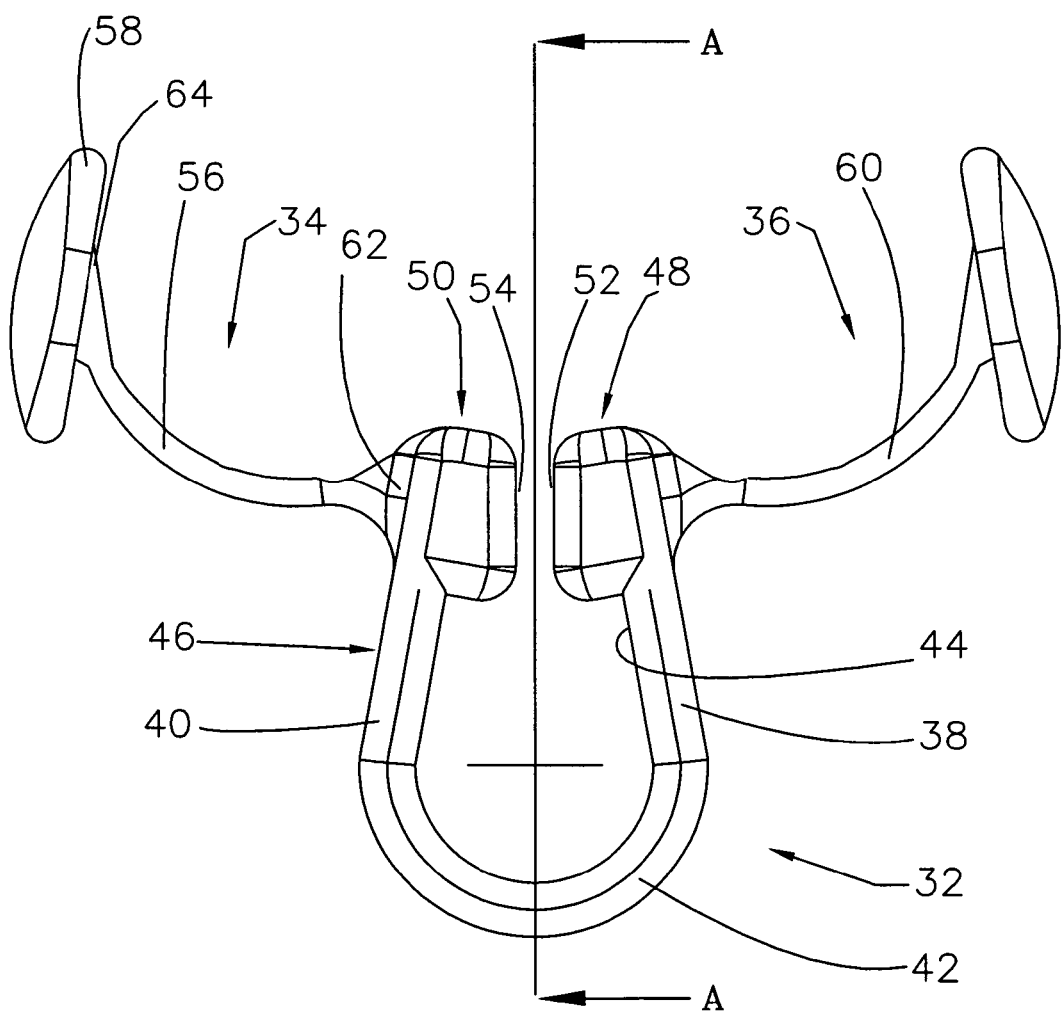
FIG. 2 is a plan view of the dilator shown in FIG. 1 in its normal condition.

More preferably, the arm 56 presents a thin planar body having a first pair of opposite major surfaces 60, and a second pair of parallel surfaces (not shown) generally perpendicular to the first. To reduce obstruction, the preferred arm 56 is oriented such that the major surfaces are parallel with the direction of airflow during respiration. At a first end 62, the arm 56 is fixedly attached to the clip 32 on the outer surface 46 near the distal end of linear portion 40. At the opposite second end 64, the arm 56 is flexibly fixed to the interior surface 66 of the disk 58. The preferred second end 64 presents an oval or circular shape as shown in FIG. 3, which further enables disk 58 flexure. However, other flexible connection configurations may be utilized, including ball-and-socket, without departing from the scope of the present invention. Also shown in FIGS. 2 and 3, the preferred first and second ends 62,64 are enlarged in comparison to the remainder of the arm 56 for increased durability. To facilitate bending, the arm 56 is preferably bowed in an arcuate shape as shown in FIG. 2.

The preferred disk 58 is configured to be comfortably inserted within the nasal passageway 24 and to evenly apply a force therein. The preferred disk 58 presents a thin slightly concave panel. As shown in the illustrated embodiment, the panel is preferably oval in shape. A circumscribing margin 68 extends continuously around the panel and is inverted towards the center of the panel, so as to present a rounded radially outermost disk portion similar to a frisbee. The disk 58 presents a surface area sufficiently sized to engage only a portion of the outer wall 28 of the nostril 20.

As best shown in FIG. 4, where delivery of medicine, drugs, or other compounds is desired the dilator 10 also includes left and right compound delivery elements 70,72 that are attached to respective expanders 34,36. The compound delivery elements 70,72 are detached, i.e. not connected to an external source, and, more particularly, are configured to store and deliver a quantity of a compound 74 to the mucosal lining 31. As used herein, the term "compound" includes elements, emulsions, suspensions, mixtures and other forms or combinations of substance suitable for use with the present invention. Furthermore, it will be appreciated that the compound may be medicinal or non-medicinal in nature, and may, in that regard, include therapeutic or aromatic substances.

More preferably, the clip 32 and delivery elements 70,72 are cooperatively configured to discharge the compound 74 at a distance not less than twenty-five percent (25%) of the overall nasal passageway length, which is where the mucosal lining 31 fully transitions from the outer epidermal. It is also appreciated by those skilled in the relevant art that numerous tiny blood vessels, or capillaries, lie just under the mucosal lining 31 of the nose, near the surface of the nasal passageways, and that delivery of the compound 74 to the lining 31 increases the efficiency of absorption into the blood stream. Most preferably, the clip 32 and delivery elements 70,72 are cooperatively configured to gradually deliver the compound 74 at a distance not less than fifty percent (50%) of total passageway length within the nose, so that compound 74 can also be absorbed by the lining 31 during exhalation.

Each of the delivery elements 70,72 preferably presents a shallow carrying receptacle 76 that defines at least one discharge opening 78. More preferably, the receptacle 76 presents a rectangular shape having filleted leading edges, so as not to damage the lining 31 during placement, and a plurality of discharge openings 78. The receptacle 76 preferably includes a flared base section 80 for greater strength of connection to the arm 56. The openings 78 are located near and the floor 82 of the receptacle 76 is preferably sloped towards the distal end of the receptacle 76, (see FIG. 5*a*) so as to promote the discharge of the compound during use.

The compound 74 and delivery elements 70,72 are configured to discharge the compound 74 over a period of time. More preferably, the compound 74 is discharged over a period of at least one hour, and, most preferably, over a period of four to twelve hours. In this regard, the preferred receptacle 76 is ideally designed for carrying a time-released paste having sufficient viscosity to effect gradual discharge through the openings 78. The paste may alternatively provide for the suspension and delivery of airborne molecules into the passageway 24. It will be appreciated by those in the art that gradually discharging the compound increases the efficiency of absorption into the blood stream, and, therefore, the effectiveness of the active ingredients. Finally, to vary the discharge rate of the compound 74 a portion of the plurality of openings 78 can be safely overlaid with an adhesive-backed cover 84. It is also well within the ambit of the present invention, however, to utilize other structures for storing and delivering a compound at the proscribed locations in conjunction with the nasal dilator 10. For example, a tubular capsule having a pervious wall or an absorbent foam could be utilized.

The compound delivery elements 70,72 are preferably formed integrally with the other dilator components. More preferably, however, the delivery elements 70,72 are removably coupled to the dilator 10, and safe-guards are incorporated to prevent unwanted dislodgment during use. As shown in FIG. 5*a,* a plurality of button probes 86 are fixedly attached to each delivery element, and a plurality of depressions 88 in the corresponding arm are concentrically alignable, so as to enable the delivery elements 70,72 and arms 56 to snap into the interfitted position shown in FIG. 5*a.* It is certainly within the ambit of the invention, however, to provide other means for securing delivery elements to the remainder of the dilator 10. For example, a small cotter pin, screw, or other type of conventional fastener that does not interfere with the function of the nose could be utilized.

The dilator 10 is formed of any suitable non-toxic, hypoallergenic, and bendably rigid natural or synthetic material. More preferably, the dilator 10 is manufactured using a synthetic polymer composition. The selected material and the configuration of the disk 58, however, is preferably such that the preferred disk 58 is inelastically bendable and therefore permanently conformable to the shape of the nostril 20. The dilator 10 is preferably constructed through conventional means, such as injection molding, and in a manner that results in seamless contact with the user. At least a portion of the dilator 10, including the septum engaging pads 50,52 and nostril engaging disks 58, can be further molded or double-dipped with a relatively soft material to present a more comfortable outer interface. More particularly, the coating material may comprise of a compressible soft foam, such as a urethane foam approximately 0.025 centimeters thick. A suitable coating may also be utilized to provide other desirable characteristics, such as fluorescence for night-time viability.

The physical state of the compound 74 may be selected from among various liquids, pastes, hard and soft gelatin capsules, solid pellets, and combinations thereof. The compound 74 itself may comprise of any one or combination of conventional nasal delivery agents, including ionic zinc, pain relief agents, antihistamines/decongestants, scenting agents, herbal supplements, insulin, growth hormones, asthma drug medication, germicides, microbicidal agents, and other beneficial agents. The compound may also include, for example, volatile oils such as eucalyptus; or the compound may be electrically charged for attracting and retaining pollen particles or other particulates and thereby extracting such particulates from the airflow; or the compound may comprise magnetic materials for providing the health benefits that some attribute to exposure to magnetic fields. Thus, it should be understood that the compound may function to add/release to or remove/extract from the air flow through the nostrils.

In operation, after selecting a dilator 10 of a suitable size for the user, the dilator 10 is installed by gently bending the expanders 34,36 inward and slightly opening the U-shaped clip to increase the distance between pads 50,52. The expanders 34,36, linear portions 38,40 of the clip 32, and pads 50,52 are then inserted through the outlets 26 of the nostrils 20,22 and released. The dilator 10 is slid further into the nostrils and adjusted as necessary to reach the desired final location. More preferably, the dilator 10 is maneuvered into place such that the vertex of the bent portion 42 is adjacent the exposed portion of the septum 16 (see FIG. 1). Once in place, the dilator 10 exerts holding and dilating forces upon the nose as it attempts to revert to its normal uncompressed condition shown in FIGS. 2 and 4. More particularly, the expanders 34,36 apply outward biasing forces to the outer walls 28 to maintain the nostrils 20,22 in the open position shown in FIG. 1, and the pads 50,52 compress the septum 16 to help breathing and reduce snoring.

Where compound delivery is desired, the compound 74 is placed within or otherwise retained by attached delivery elements 70,72, prior to installation of the dilator 10. The compound 74 gradually discharges from the elements 70,72 over a period of at least one hour, and, most preferably, over a period of four to twelve hours. Once the compound 74 is depleted and dilation is no longer desired, the dilator 10 can be removed and stored in a sanitized environment or simply disposed of. If stored, the dilator 10 can be reused by replacing the dissipated compound with a second quantity and re-installing the dilator 10, though this ability will depend on the manner in which the compound is applied to the dilator 10.

In a second preferred embodiment of the present invention, dilator 100 is shown with a different configuration, particularly with regard to the expanders 102,104 (see FIGS. 6 through 9). Dilator 100 may be similar to dilator 10 in all aspects including material composition, manufacture and modes of operation, except for the following modifications, and, as such, only those aspects of dilator 100 differing from dilator 10 will be further described in detail herein.

Figure 6:
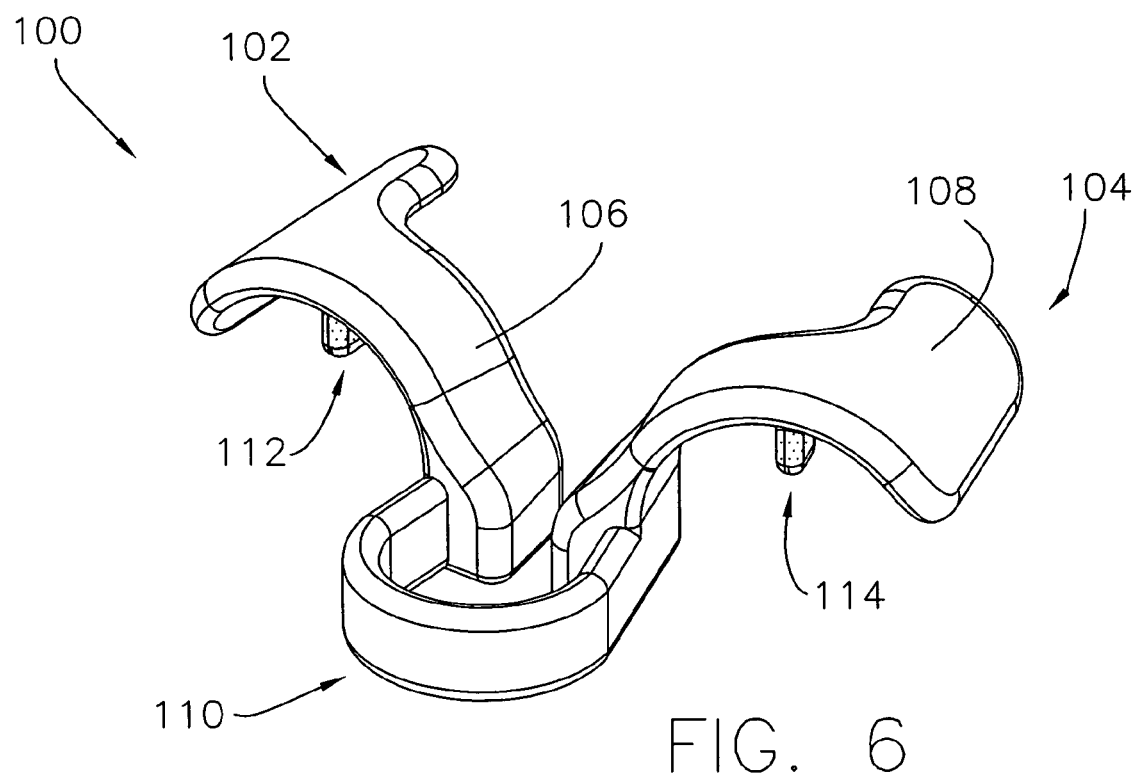
FIG. 6 is a perspective view of an internal nasal dilator constructed in accordance with a second preferred embodiment of the present invention.
Figure 7:
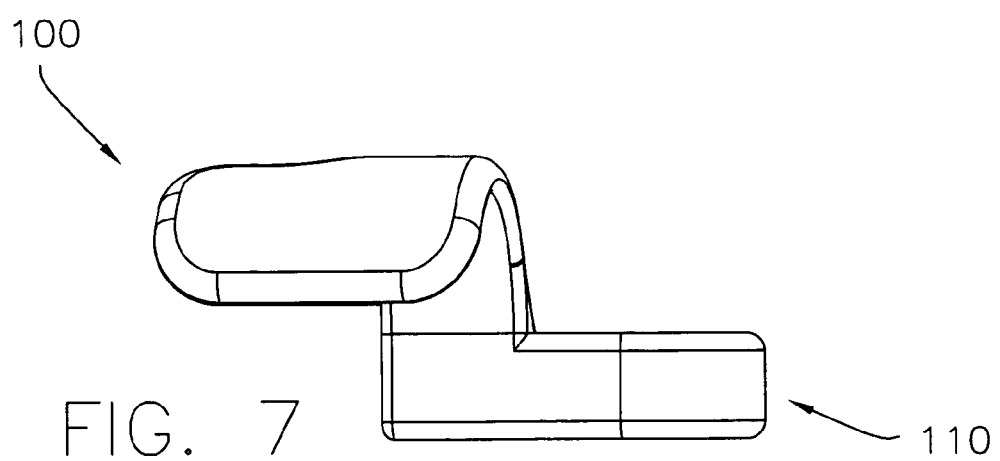
FIG. 7 is a side-elevational view of the dilator shown in FIG. 6.

As shown in FIG. 6, each of the preferably integrally formed expanders 102,104 presents an arm portion 106 spaced from the nostrils 20,22, and a nostril engaging portion 108 adjacent to the distal end of the arm portion 106. Like the expanders 34,36 of the first embodiment, the expanders 102,104 of the second embodiment preferably present thin planar bodies having first pairs of opposite major surfaces, and second pairs of parallel surfaces (not shown) perpendicular to the first pairs. The major surfaces of the nostril engaging portions 108 preferably present greater lateral widths than do the major surfaces of the arm portions 106 in order to more broadly apply the dilating force to the nostril. The arm portions 106 are preferably oriented such that the major surfaces are parallel with the direction of air-flow during respiration.

As best shown in FIG. 6, the arm portion 106 is fixedly attached to a U-shaped clip 110 similar to the clip 32 of the first embodiment. However, unlike the dilator 10 of the first embodiment, the preferred expanders 102,104 are fixedly attached to the top surface of the linear portions of the clip 110 and pads, and generally project diagonally outward toward two and ten o'clock positions in the normal condition. More preferably, the expanders 102,104 generally project from the top surface of the clip 110 at an approximately forty-five degree vertical angle from horizontal. It is appreciated that where the flexible outer wall 28 defines a quarter circle between the face and septum 16 of the user, maximum dilation is achieved by orienting the dilating force vector in this direction.

Figure 8:
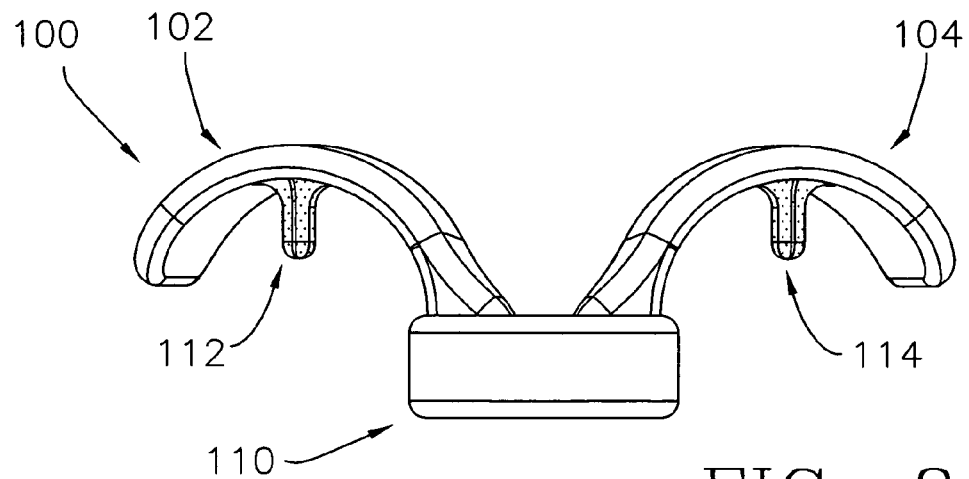
FIG. 8 is a front-elevational view of the dilator shown in FIGS. 6 and 7, particularly showing two compound delivery elements.

The arm portions 106 preferably present upwardly bowed sections so as to promote bending and the application of a biasing force in a bent or flexed condition. As best shown in FIG. 8, the bowed sections more preferably extend along the entire length of the expanders 102,104, so that the expanders 102,104 present half circular or elliptical arcuate elevations. Also shown in FIGS. 6 and 8, the fixed ends of the expanders 102,104 are thicker in comparison to the remainder of the arm portions 106 for increased durability. The fixed end of each expander 102,104 overlays and stems from the full top surface width of a pad and a section of a linear portion of the clip 110 adjacent its distal end. Finally, the dilator 100 preferably presents filleted edges and rounded corners so as to prevent scraping and other damage to the mucosal lining 31 (see FIGS. 6 and 9) during insertion and removal.

Figure 9:
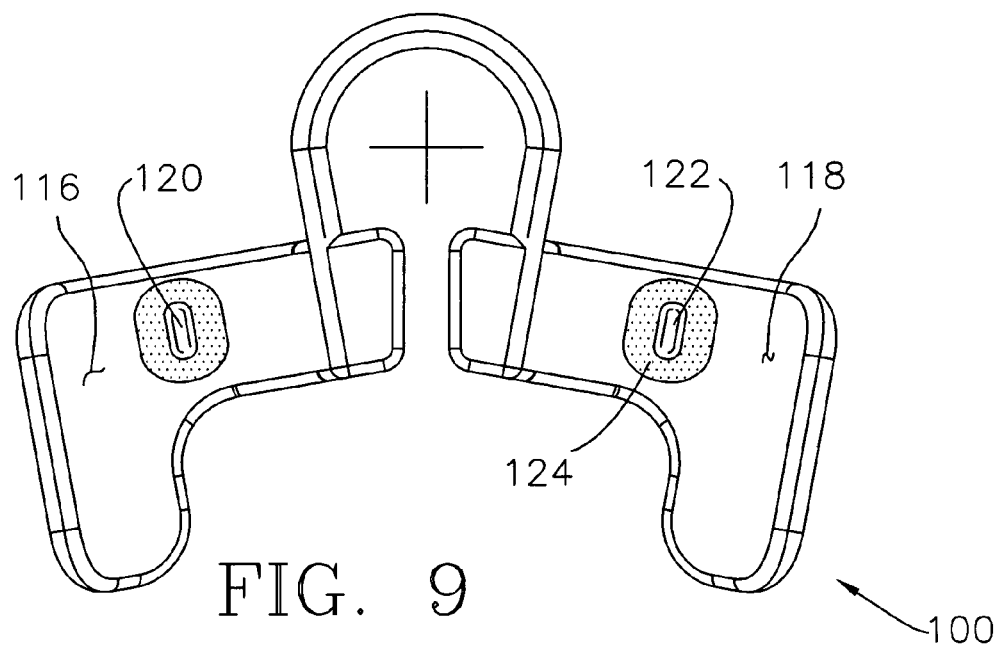
FIG. 9 is a plan view of the dilator shown in FIGS. 6 through 8 in its normal condition, particularly showing the compound delivery elements and septum engaging pads.

In the illustrated embodiment shown in FIGS. 6 through 9, the expanders 102,104 are also upwardly bowed to facilitate proper functioning of the compound delivery elements 112,114. As best shown in FIG. 9, the preferred delivery elements 112,114 are affixed to the lower surfaces 116,118 of the expanders 102,104, respectively. The preferred elements 112,114 present cylindrical prongs 120,122 that project toward the face of the user during use and generally perpendicular to the direction of air-flow during respiration. It will be appreciated that this configuration provides maximum interaction between the elements 112, 114 and air-flow. The prongs 120,122 are each configured so as not to contact the mucosal lining 31 during use, and, more preferably, presents a length of approximately less than one centimeter.

Figure 9A:
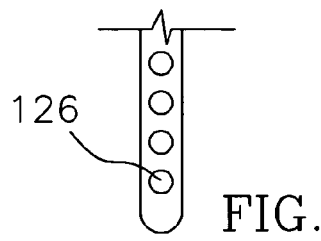
FIG. 9a is fragmentary side elevational view of a compound delivery element prong defining a plurality of openings.
Figure 9B:
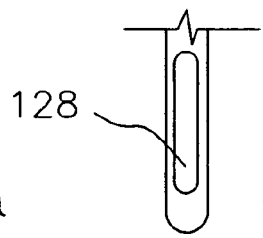
FIG. 9b is a fragmentary side elevational view of a compound delivery element prong defining a continuous slot.

As shown in FIG. 9, prongs 120,122 are configured to receive and retain a quantity of a medicinal, therapeutic, aromatic, drug, or other compound 124. Each of the prongs 120,122 preferably presents a plurality of openings 126, or, alternatively, a continues open slot 128, (see FIGS. 9a,b) that aid in retaining the compound 124 on the prongs 120,122. More specifically, the compound 124 is preferably applied to and received on the prongs 120,122 in such a manner that the compound substantially covers the prongs 120,122 and passes completely through the prongs 120,122 at the locations of the openings 126 or slots 128. That portion of the compound 124 that passes through openings 126 or slots 128 acts as a structural retention mechanism to aid in retaining the compound on the prongs 120,122.

While the material composition and manufacture of the dilator 100 of the second embodiment is similar to the dilator 10 of the first, the formation of the compound 124 onto the prongs 120,122 can be accomplished by any conventional means including injection molding, hot molding, manual dipping or the like. More preferably, the method of formation comprises the steps of providing the compound 124 in liquid or paste form, providing two cavity molds, or negative molds, configured to form and release a product of desired dimension, inserting prongs 120,122 within the molds, placing the compound within the molds and adjacent the prongs 120,122, and allowing the compound to solidify and adhere to the prongs 120,122 over a period of time.

Most preferably, the prongs are inserted completely within the molds, such that the molds abut the lower surfaces 116,118 of the expanders 102,104, and the compound solidifies at room temperature, i.e., approximately seventy-three degrees Fahrenheit, and approximately sixty-five percent humidity within a period of four hours. Where desired, a catalyst may be added to the compound to accelerate the rate of curing to approximately thirty minutes or less, a releasing agent may be added to the mold to facilitate removal of the cast, and a primer may be added to the prong surface to facilitate adhesion. Finally, introduction of the compound and prongs into the molds is most preferably at least partially performed by conventional mechanical means, such as a suitable injection molding machine. It will be appreciated by those ordinarily skilled in the art that other desirable additives can be added to the compound; that any suitable conventional curative, catalyst, releasing agent, or primer effective for the intended purposes described may be utilized; and that the utilization of mechanical means reduces manufacturing errors and increases productivity.

Where hot molding is utilized in formation, the process may include the steps of providing the compound 124 in a solid form, such as pellets or capsules, heating the molds to a temperature in excess of the melting point of the solid compound 124, allowing the compound 124 to liquify prior to inserting the prongs 120,122, and providing an additional cool-down period to reduce the temperature of the compound 124. More preferably, a cool-down period of not less than approximately one-hour is provided, while the molds and compound 124 are exposed to a suitable cooling source (not shown) configured to accelerate the rate of temperature loss. It should be noted that in order to enable its proper function, the compound 124 must have a melting point measurably greater than room temperature but less than the temperature typically present within the nasal passageway 24, and more preferably approximately between the range of 80° and 90° F.

In operation, the prongs 120,122 and the compound 124 are cooperatively configured to deliver the beneficial agent to the user at a gradual rate and over a desired period of time by melting the compound so that the agent directly contacts the lining 31, by sublimation wherein the compound 124 releases airborne particles into the nasal cavity 14, or a combination of the two.

Figure 10:
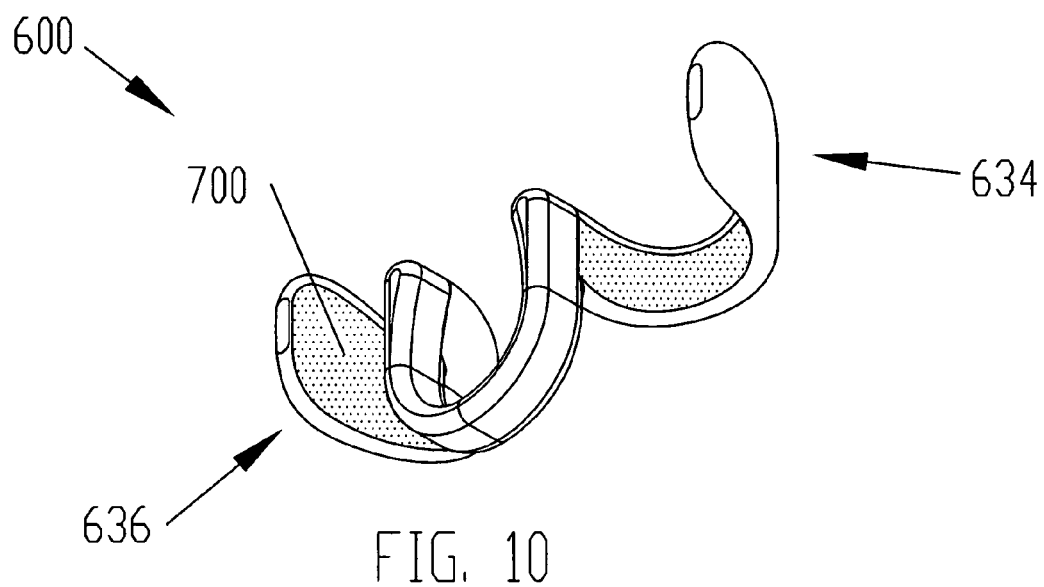
FIG. 10 is an isometric view of the internal nasal dilator constructed in accordance with a second preferred embodiment of the present invention.
Figure 11:
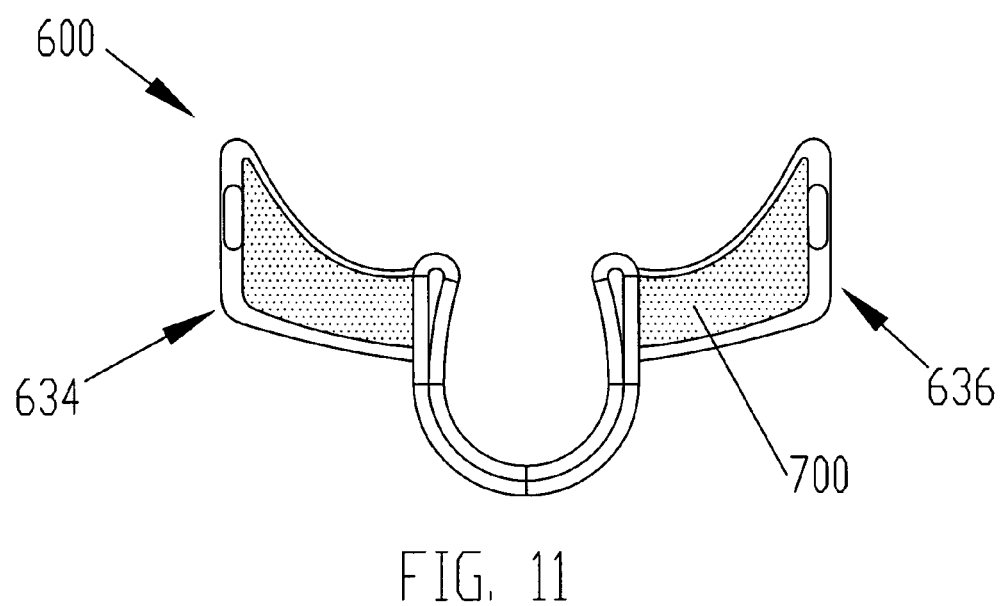
FIG. 11 is a plan view of the dilator shown in FIG. 10.

Referring to FIGS. 10 and 11, a second preferred embodiment of the nasal dilator 600 is shown which may be substantially similar or identical to the above-described first preferred embodiment but for the following differences. Rather than supporting the compound on a projecting structure, the compound is present in the form of an overlay 700, such as a film, overmolded in the manner described above or otherwise applied to the inner surfaces of the left and right nasal expanders 634,636. The thickness of the overlay 700 may vary depending on such factors as the nature and characteristics of the particular compound. It is contemplated, however, that, at least for some compounds, the overlay 700 may be approximately 0.001 inches to 0.100 inches in thickness. The overlay 700 may comprise a suitable base, or carrier, such as glycerin, glycerol, or sodium hydroxide, which evaporates into the airflow within the nostrils; the compound may be suspended in the base so as to be released as the base evaporates. Use of a base provides one way of controlling the rate at which the compound is released, either by changing the formula of the base to control the evaporation rate or by changing the concentration of the compound suspended in the base. Alternatively, the overlay 700 may include no base, in which case the overlay 700 will be substantially or entirely the compound itself.

For example, an inhalable version of an antibiotic tobramycin solution (Tobi®) has been approved for use in suppressing pseudomonas aeruginosa in the airways of patients with cystic fibrosis. Currently, the drug is aerosolized, or converted into a fine mist using a nebulizer device so that it can be inhaled into the lungs. A nebulizer is a relatively complex and expensive device, and includes a mouthpiece or mask and an electrically-powered air compressor. The present invention provides a less expensive, less complex, and more consistent and longer delivery mechanism for drugs such as Tobi® and other inhalables, including bronchodilators (airway-opening) medications.

Additionally, it will be appreciated that moisture may be suspended in the base or carrier, such that the evaporating base releases the moisture and, in effect, humidifies the air flow into the lungs.

The preferred forms of the present invention and modes of operation described above are to be considered illustrative only, and should not be utilized in a limiting sense in interpreting the scope of the present invention. Obvious modifications to the exemplary embodiments, as set forth above, could be readily made by those skilled in the relevant arts without departing from the spirit of the present invention or the contemplated scope of protection.

The inventor hereby states his intent to rely on the Doctrine of Equivalents to determine and assess the reasonably fair scope of the present invention as pertains to any apparatus not materially departing from but outside the literal scope of the invention as set forth in the following claims.

What is claimed is:

1. An internal nasal dilator for use within a nose having first and second nostrils separated by a septum, each of the nostrils defining in part an internal nasal passageway and an interior outer wall surface generally opposite the septum, the dilator comprising:
   a clip configured to contract and apply an inward force to the septum when the dilator is donned, wherein the clip contacts the septum along first and second planar engaging surfaces;
   first and second nostril expanders, with each of the nostril expanders including—
      a nostril engaging element configured to contact and exert an outward force against a portion of the interior outer wall surface of a respective nostril when the dilator is donned, and
      an arm interconnecting the nostril engaging element and the clip; and
   a film including a compound disposed on at least a portion of a surface of the first and second nostril expanders.

2. The internal nasal dilator as claimed in claim 1, wherein the surface on which the compound is disposed is exposed to an airflow within the nostrils.

3. The internal nasal dilator as claimed in claim 2, wherein the compound releases into the airflow.

4. The internal nasal dilator as claimed in claim 2, wherein the compound is released through evaporation over time into the airflow.

5. The internal nasal dilator as claimed in claim 2, wherein the compound functions to extract a material from the airflow.

6. The internal nasal dilator as claimed in claim 1, wherein the compound is a medicinal agent.

7. The internal nasal dilator as claimed in claim 1, wherein the film is approximately between 0.001 inches and 0.100 inches in thickness.

8. The internal nasal dilator as claimed in claim 1, wherein the compound is suspended within a base.

9. The internal nasal dilator as claimed in claim 8, wherein the base comprises glycerin.

10. An internal nasal dilator for use within a nose having first and second nostrils separated by a septum, each of the nostrils defining in part an internal nasal passageway and an interior outer wall surface generally opposite the septum, the dilator comprising:
   a clip configured to contract and apply an inward force to the septum when the dilator is donned, wherein the clip contacts the septum along first and second planar engaging surfaces;
   first and second nostril expanders with each of the nostril expanders including—
      a nostril engaging element configured to contact and exert an outward force against a portion of the interior outer wall surface of a respective nostril when the dilator is donned, and
      an arm interconnecting the nostril engaging element and the clip; and
   a film including a compound disposed on at least a portion of a surface of the first and second nostril expanders which is exposed to an airflow within the nostrils, wherein the film is approximately between 0.001 inches and 0.100 inches in thickness.

11. The internal nasal dilator as claimed in claim 10, wherein the compound releases into the airflow.

12. The internal nasal dilator as claimed in claim 10, wherein the compound is released through evaporation over time into the airflow.

13. The internal nasal dilator as claimed in claim 10, wherein the compound functions to extract a material from the airflow.

14. The internal nasal dilator as claimed in claim 10, wherein the compound is a medicinal agent.

15. The internal nasal dilator as claimed in claim 10, wherein the compound is suspended within a base.

16. The internal nasal dilator as claimed in claim 15, wherein the base comprises of glycerin.

17. An internal nasal dilator for use within a nose having first and second nostrils separated by a septum, each of the nostrils defining in part an internal nasal passageway and an interior outer wall surface generally opposite the septum, the dilator comprising:
   a clip configured to contact and apply an inward force to the septum when the dilator is donned, wherein the clip contacts the septum along first and second planar engaging surfaces;
   first and second nostril expanders, with each of the nostril expanders including—
      a nostril engaging element configured to contact an exert an outward force against a portion of the interior outer wall surface of a respective nostril when the dilator is donned, and
      an arm interconnecting the nostril engaging element and the clip; and
   a film including a compound suspended in a base and disposed on at least a portion of a surface of the first and second nostril expanders which is exposed to an airflow within the nostrils, wherein the base comprises glycerin, and wherein the film is approximately between 0.001 inches and 0.100 inches in thickness.

18. The internal nasal dilator as claimed in claim 17, wherein the compound is released through evaporation over time into the airflow.

19. The internal nasal dilator as claimed in claim 17, wherein the compound functions to extract a material from the airflow.

20. The internal nasal dilator as claimed in claim 17, wherein the compound is a medicinal agent.

* * * * *